(12) United States Patent
Wright

(10) Patent No.: US 8,162,898 B1
(45) Date of Patent: Apr. 24, 2012

(54) VENIPUNCTURE BASE PLATE ASSEMBLY AND METHOD OF USING SAME

(75) Inventor: Clifford A. Wright, San Diego, CA (US)

(73) Assignee: Venetec International, Inc., Covington, GA (US)

( * ) Notice: Subject to any disclaimer, the term of this patent is extended or adjusted under 35 U.S.C. 154(b) by 1915 days.

(21) Appl. No.: 11/109,480

(22) Filed: Apr. 18, 2005

(51) Int. Cl.
*A61M 5/32* (2006.01)

(52) U.S. Cl. ........ 604/180; 604/175; 604/176; 604/332; 604/344; 604/174; 604/177; 604/178; 604/179; 24/269

(58) Field of Classification Search .................. 24/269; 604/93, 165, 332, 344, 174–180
See application file for complete search history.

(56) References Cited

U.S. PATENT DOCUMENTS

| | | | |
|---|---|---|---|
| 1,706,634 A | 3/1928 | Seils | |
| 2,367,690 A | 7/1943 | Purdy | |
| 2,525,398 A | 2/1950 | Collins | |
| 2,533,961 A | 12/1950 | Rousseau et al. | |
| 2,707,953 A | 5/1955 | Ryan | |
| 3,059,645 A | 10/1962 | Hasbrouck et al. | |
| 3,064,648 A | 11/1962 | Bujan | |
| 3,167,072 A | 1/1965 | Stone et al. | |
| 3,288,137 A | 11/1966 | Lund | |
| 3,482,569 A | 12/1969 | Raffaelli | |
| 3,529,597 A | 9/1970 | Fuzak | |
| 3,602,227 A | 8/1971 | Andrew | |
| 3,630,195 A | 12/1971 | Santomieri | |
| 3,677,250 A | 7/1972 | Thomas | |
| 3,766,915 A | 10/1973 | Rychlik | |
| 3,834,380 A | 9/1974 | Boyd | |
| 3,847,370 A | 11/1974 | Engelsher | |
| 3,856,020 A | 12/1974 | Kovac | |
| 3,868,030 A * | 2/1975 | Bell | 414/534 |
| 3,896,527 A | 7/1975 | Miller et al. | |
| 3,900,026 A * | 8/1975 | Wagner | 128/888 |
| 3,901,226 A | 8/1975 | Scardenzan | |
| 3,906,946 A | 9/1975 | Nordstrom | |
| 3,910,538 A | 10/1975 | Baitella | |
| 3,942,228 A | 3/1976 | Buckman et al. | |
| 3,973,565 A | 8/1976 | Steer | |

(Continued)

FOREIGN PATENT DOCUMENTS

CA          995 995          8/1976

(Continued)

OTHER PUBLICATIONS

U.S. Appl. No. 11/022,714, filed Dec. 27, 2004.

(Continued)

*Primary Examiner* — Nicholas Lucchesi
*Assistant Examiner* — Scott Medway
(74) *Attorney, Agent, or Firm* — Knobbe Martens Olson & Bear LLP

(57) ABSTRACT

A venipuncture base plate assembly includes an adapter and a patient interface platform. The adapter has a substantially flat retention clip and a platform coupled to the retention clip with two or more posts mounted on it. The patient interface platform includes a base pad having a bottom surface coated with an adhesive substance and a base unit coupled to the base pad. The base unit includes a base plate and a retainer mounted on the base plate that supports the adapter at two or more variable angles relative to the base plate.

13 Claims, 8 Drawing Sheets

U.S. PATENT DOCUMENTS

| | | | |
|---|---|---|---|
| 4,020,835 A | 5/1977 | Nordstrom et al. | |
| 4,057,066 A | 11/1977 | Taylor | |
| 4,059,105 A | 11/1977 | Cutruzzula et al. | |
| 4,082,094 A | 4/1978 | Dailey | |
| 4,114,618 A | 9/1978 | Vargas | |
| 4,129,128 A | 12/1978 | McFarlane | |
| 4,133,307 A | 1/1979 | Ness | |
| 4,142,527 A | 3/1979 | Garcia | |
| 4,161,177 A | 7/1979 | Fuchs | |
| 4,193,174 A | 3/1980 | Stephens | |
| 4,212,297 A * | 7/1980 | Frosch et al. | 128/207.14 |
| 4,224,937 A | 9/1980 | Gordon | |
| 4,248,229 A | 2/1981 | Miller | |
| 4,250,880 A | 2/1981 | Gordon | |
| 4,277,102 A | 7/1981 | Aras | |
| 4,316,461 A | 2/1982 | Marais et al. | |
| 4,324,236 A | 4/1982 | Gordon et al. | |
| 4,326,519 A | 4/1982 | D'Alo et al. | |
| 4,333,468 A | 6/1982 | Geist | |
| 4,362,156 A | 12/1982 | Feller, Jr. et al. | |
| 4,392,853 A | 7/1983 | Muto | |
| 4,397,647 A | 8/1983 | Gordon | |
| 4,435,175 A * | 3/1984 | Friden | 604/177 |
| 4,449,975 A | 5/1984 | Perry | |
| 4,453,933 A | 6/1984 | Speaker | |
| 4,474,559 A | 10/1984 | Steiger | |
| 4,480,639 A | 11/1984 | Peterson et al. | |
| 4,516,968 A | 5/1985 | Marshall et al. | |
| 4,517,971 A | 5/1985 | Sorbonne | |
| 4,563,177 A | 1/1986 | Kamen | |
| 4,633,863 A | 1/1987 | Filips et al. | |
| 4,645,492 A | 2/1987 | Weeks | |
| 4,650,473 A | 3/1987 | Bartholomew et al. | |
| 4,660,555 A | 4/1987 | Payton | |
| 4,679,553 A | 7/1987 | Proulx | |
| 4,711,636 A | 12/1987 | Bierman | |
| 4,733,661 A * | 3/1988 | Palestrant | 606/108 |
| 4,742,824 A | 5/1988 | Payton et al. | |
| 4,762,513 A | 8/1988 | Choy et al. | |
| 4,769,010 A * | 9/1988 | Fenton et al. | 604/180 |
| 4,781,695 A | 11/1988 | Dalton | |
| 4,808,162 A | 2/1989 | Oliver | |
| 4,823,789 A | 4/1989 | Beisang, III | |
| 4,826,466 A | 5/1989 | Palsrok et al. | |
| 4,846,807 A | 7/1989 | Safadago | |
| 4,852,844 A | 8/1989 | Villaveces | |
| 4,857,058 A | 8/1989 | Payton | |
| 4,863,432 A | 9/1989 | Kvalo | |
| 4,869,465 A | 9/1989 | Yirmiyahu et al. | |
| 4,870,976 A | 10/1989 | Denny | |
| 4,880,412 A | 11/1989 | Weiss | |
| 4,896,465 A | 1/1990 | Rhodes et al. | |
| 4,897,082 A | 1/1990 | Erskine | |
| 4,898,587 A | 2/1990 | Mera | |
| 4,913,393 A | 4/1990 | Wood | |
| 4,919,654 A | 4/1990 | Kalt | |
| 4,932,943 A | 6/1990 | Nowak | |
| 4,944,728 A | 7/1990 | Carrell et al. | |
| 4,952,207 A | 8/1990 | Lemieux | |
| 4,955,864 A | 9/1990 | Hajduch | |
| 4,976,698 A | 12/1990 | Stokley | |
| 4,976,700 A | 12/1990 | Tollini | |
| 4,997,421 A | 3/1991 | Palsrok et al. | |
| 5,000,741 A | 3/1991 | Kalt | |
| 5,029,941 A | 7/1991 | Twisselmann | |
| 5,037,397 A | 8/1991 | Kalt et al. | |
| 5,054,723 A * | 10/1991 | Arnold | 248/65 |
| 5,073,166 A | 12/1991 | Parks et al. | |
| 5,073,170 A | 12/1991 | Schneider | |
| 5,074,847 A | 12/1991 | Greenwell et al. | |
| 5,084,026 A | 1/1992 | Shapiro | |
| 5,098,399 A | 3/1992 | Tollini | |
| 5,112,313 A | 5/1992 | Sallee | |
| 5,116,324 A | 5/1992 | Brierley et al. | |
| 5,137,519 A * | 8/1992 | Littrell et al. | 604/174 |
| 5,147,322 A | 9/1992 | Bowen et al. | |
| 5,156,641 A | 10/1992 | White | |
| 5,167,240 A | 12/1992 | Rozier et al. | |
| 5,192,273 A | 3/1993 | Bierman | |
| 5,192,274 A | 3/1993 | Bierman | |
| 5,195,981 A | 3/1993 | Johnson | |
| 5,226,892 A | 7/1993 | Boswell | |
| 5,238,010 A | 8/1993 | Grabenkort et al. | |
| 5,266,401 A | 11/1993 | Tollini | |
| 5,267,967 A | 12/1993 | Schneider | |
| 5,281,001 A | 1/1994 | Bergsten et al. | |
| 5,282,463 A | 2/1994 | Hammersley | |
| 5,292,312 A | 3/1994 | Delk et al. | |
| 5,304,146 A | 4/1994 | Johnson et al. | |
| 5,306,243 A | 4/1994 | Bonaldo | |
| 5,314,411 A | 5/1994 | Bierman | |
| 5,322,514 A | 6/1994 | Steube et al. | |
| 5,330,438 A | 7/1994 | Gollobin et al. | |
| 5,338,308 A | 8/1994 | Wilk | |
| 5,339,834 A | 8/1994 | Marcelli | |
| 5,342,317 A | 8/1994 | Claywell | |
| 5,344,406 A | 9/1994 | Spooner | |
| 5,344,414 A | 9/1994 | Lopez et al. | |
| 5,346,479 A | 9/1994 | Schneider | |
| 5,352,211 A | 10/1994 | Merskelly | |
| 5,354,282 A | 10/1994 | Bierman | |
| 5,354,283 A | 10/1994 | Bark et al. | |
| 5,380,293 A | 1/1995 | Grant | |
| 5,380,294 A | 1/1995 | Persson | |
| 5,380,301 A | 1/1995 | Prichard et al. | |
| 5,382,239 A | 1/1995 | Orr et al. | |
| 5,382,240 A | 1/1995 | Lam | |
| 5,389,082 A | 2/1995 | Baugues et al. | |
| 5,395,344 A | 3/1995 | Beisang, III et al. | |
| 5,403,285 A | 4/1995 | Roberts | |
| 5,405,110 A * | 4/1995 | Mistretta | 248/122.1 |
| 5,407,249 A | 4/1995 | Bonutti | |
| 5,413,120 A | 5/1995 | Grant | |
| 5,413,562 A | 5/1995 | Swauger | |
| 5,443,460 A | 8/1995 | Milusek | |
| 5,449,349 A | 9/1995 | Sallee et al. | |
| 5,456,671 A | 10/1995 | Bierman | |
| 5,462,247 A | 10/1995 | Aldrich | |
| 5,468,228 A | 11/1995 | Gebert | |
| 5,468,230 A | 11/1995 | Corn | |
| 5,468,231 A | 11/1995 | Newman et al. | |
| 5,470,321 A | 11/1995 | Forster et al. | |
| D364,922 S | 12/1995 | Bierman | |
| 5,147,322 A | 1/1996 | Bowen et al. | |
| 5,484,420 A | 1/1996 | Russo | |
| 5,496,282 A | 3/1996 | Militzer et al. | |
| 5,496,283 A | 3/1996 | Alexander | |
| 5,499,976 A | 3/1996 | Dalton | |
| 5,520,656 A | 5/1996 | Byrd | |
| 5,522,803 A | 6/1996 | Teissen-Simony | |
| 5,527,293 A | 6/1996 | Zamierowski | |
| 5,549,567 A | 8/1996 | Wolman | |
| D375,355 S | 11/1996 | Bierman | |
| D377,125 S | 1/1997 | Adamsson | |
| 5,638,814 A | 6/1997 | Byrd | |
| 5,690,616 A | 11/1997 | Mogg | |
| 5,697,907 A | 12/1997 | Gaba | |
| 5,702,371 A * | 12/1997 | Bierman | 604/180 |
| 5,713,591 A | 2/1998 | Zarkhin et al. | |
| 5,722,959 A | 3/1998 | Bierman | |
| 5,738,660 A | 4/1998 | Luther | |
| 5,776,106 A | 7/1998 | Matyas | |
| 5,795,335 A | 8/1998 | Zinreich | |
| 5,800,402 A | 9/1998 | Bierman | |
| 5,885,254 A | 3/1999 | Matyas | |
| 6,001,081 A | 12/1999 | Collen | |
| 6,027,480 A | 2/2000 | Davis et al. | |
| 6,039,725 A * | 3/2000 | Moenning et al. | 606/1 |
| 6,132,398 A * | 10/2000 | Bierman | 604/174 |
| 6,213,979 B1 | 4/2001 | Bierman | |
| 6,231,547 B1 | 5/2001 | O'Hara | |
| 6,322,539 B1 | 11/2001 | Cook | |
| 6,332,874 B1 | 12/2001 | Eliasen et al. | |
| 6,447,485 B2 | 9/2002 | Bierman | |
| 6,491,664 B2 * | 12/2002 | Bierman | 604/180 |
| 6,582,403 B1 | 6/2003 | Bierman et al. | |
| 6,585,703 B1 | 7/2003 | Kassel et al. | |

| | | | |
|---|---|---|---|
| 6,619,598 B2 | 9/2003 | De Miranda | |
| 6,619,747 B2 | 9/2003 | Ko et al. | |
| 6,827,707 B2 | 12/2004 | Wright et al. | |
| 6,872,194 B2 | 3/2005 | Doyle et al. | |
| 6,984,145 B1 | 1/2006 | Lim et al. | |
| 7,247,150 B2 | 7/2007 | Bierman | |
| 7,569,034 B2 * | 8/2009 | Lynch et al. | 604/174 |
| 2004/0035431 A1 | 2/2004 | Wright | |
| 2004/0139973 A1 | 7/2004 | Wright | |
| 2004/0158209 A1 | 8/2004 | Wright | |
| 2004/0204685 A1 | 10/2004 | Wright | |
| 2005/0016542 A1 | 1/2005 | Wright | |
| 2005/0052066 A1 | 3/2005 | Wright | |

FOREIGN PATENT DOCUMENTS

| | | |
|---|---|---|
| CA | 2 281 457 | 2/2001 |
| DE | 2341297 | 8/1973 |
| EP | 0064284 A2 | 11/1982 |
| EP | 0247590 A2 | 12/1987 |
| EP | 20247590 | 12/1987 |
| EP | 0356683 A | 3/1990 |
| FR | 1 184 139 A | 7/1959 |
| FR | 2 381 529 | 9/1978 |
| GB | 2063679 | 11/1980 |
| GB | 2 086 466 A | 5/1982 |
| JP | 63-211700 | 9/1988 |
| JP | 02-93530 | 4/1990 |
| JP | 04-51767 | 4/1992 |
| JP | 06-344852 | 12/1994 |
| JP | 1995-28563 | 5/1995 |
| WO | WO 80/01458 | 7/1980 |
| WO | WO 85/02774 | 7/1985 |
| WO | WO 91/16939 | 11/1991 |
| WO | WO 92/19309 | 11/1992 |
| WO | WO 96/10435 | 4/1996 |
| WO | WO 98/53872 | 12/1998 |
| WO | WO 99/25399 | 5/1999 |

OTHER PUBLICATIONS

U.S. Appl. No. 11/073,409, filed Mar. 4, 2005.
U.S. Appl. No. 11/089,980, filed Mar. 24, 2005.
U.S. Appl. No. 11/109,465, filed Apr. 18, 2005.
U.S. Appl. No. 11/110,986, filed Apr. 19, 2005.
U.S. Appl. No. 60/662,177, filed Mar. 15, 2005.
Venetec Statlock Instructional Sheets; statlock.com/products.html; "IV Select; IV Ultra; IV Plus; IV; Intima; IV-K; Arterial Plus; CV Plus; CV Ultra; The Advantages of Statlock for Extended-Dwell Catheters; PICC Plus Patient User Guide;".
Multiple-Lumen Central Venous Catheterizatlon Product With ARROW+gard™ Antiseptic Surface (Arrow International brochure) (Apr. 1994).
Photographs (4) of Catheter Clamp and Rigid Fastener sold by Arrow International. Inc.

* cited by examiner

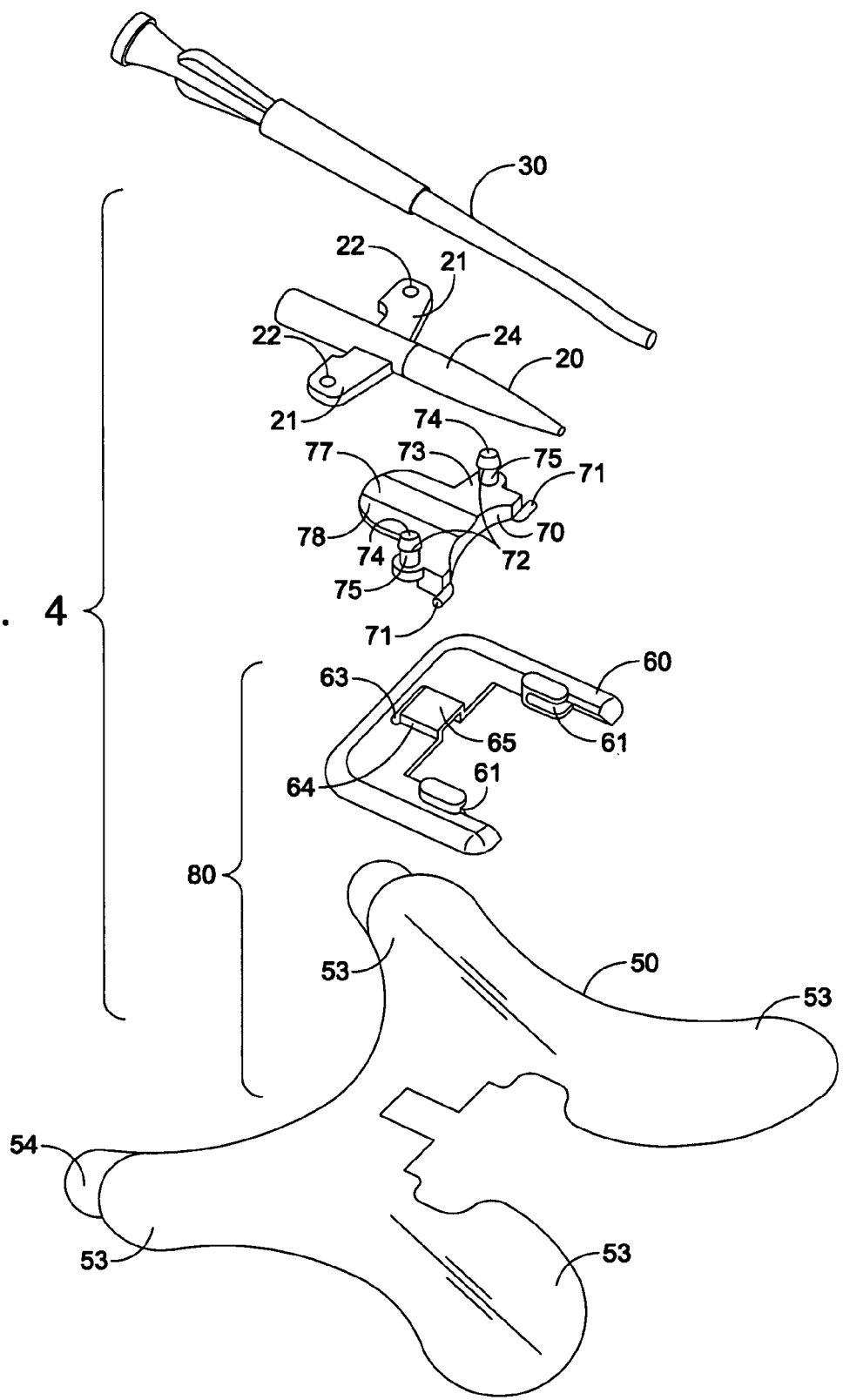

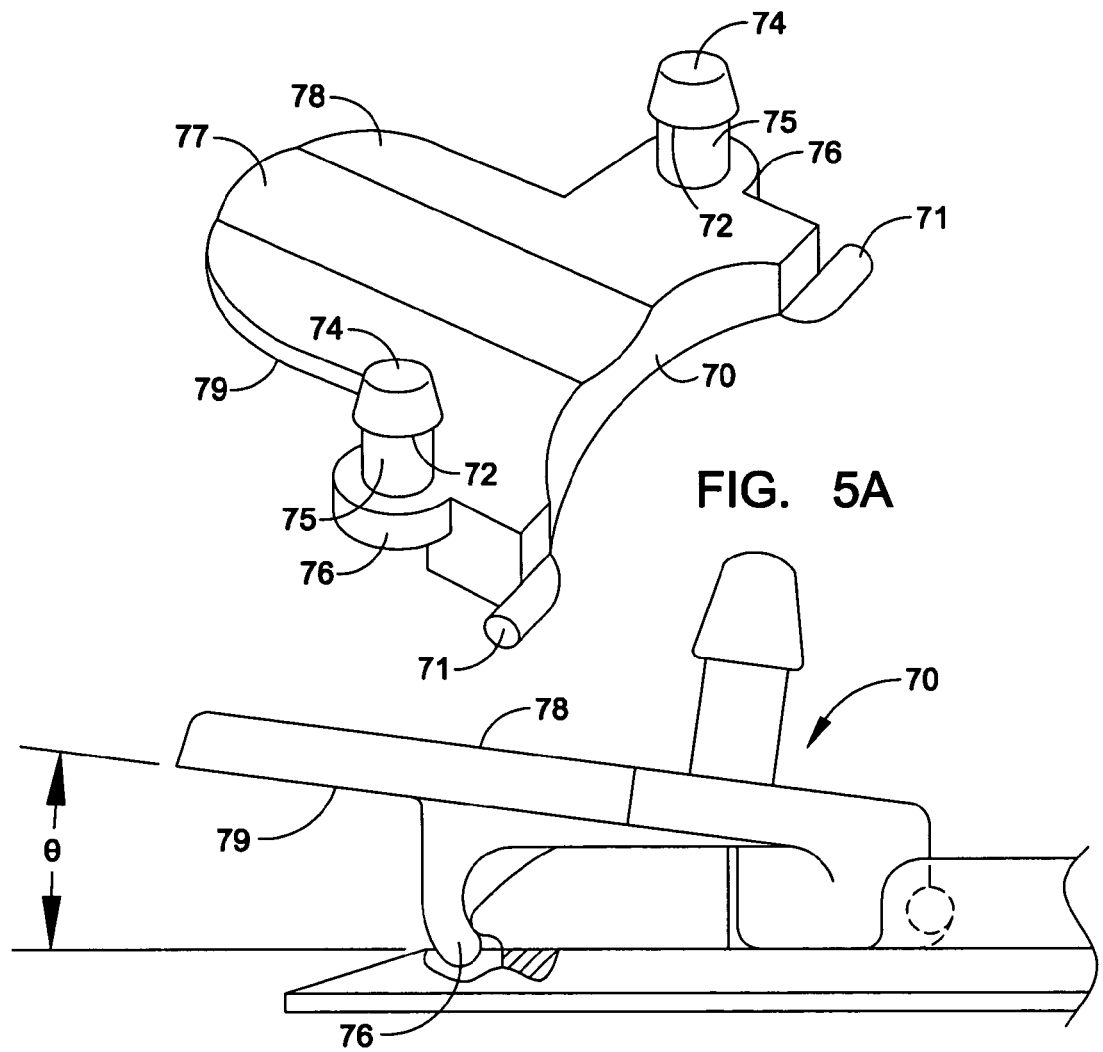
FIG. 5A
FIG. 5B
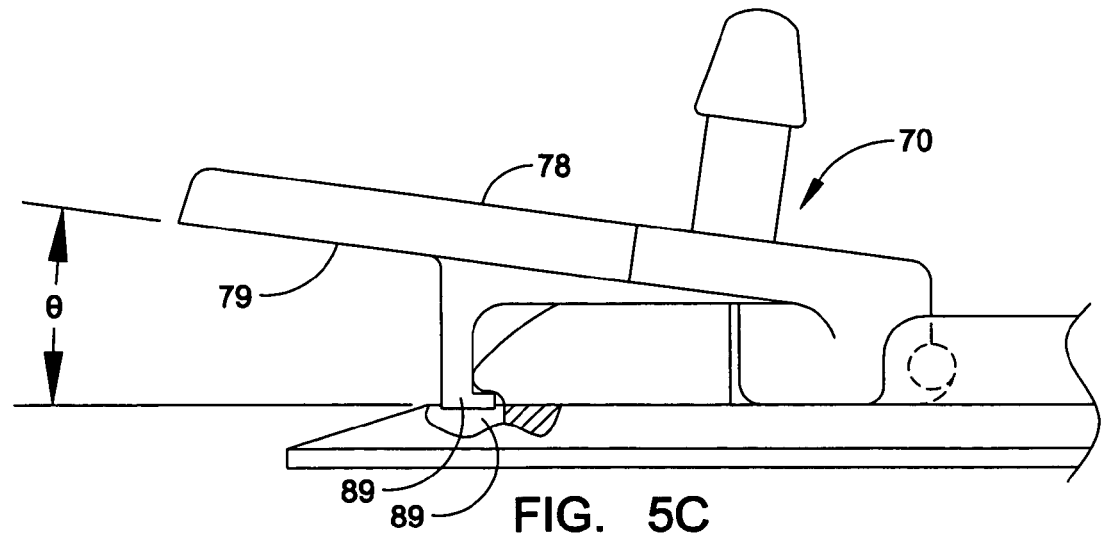
FIG. 5C

VENIPUNCTURE BASE PLATE ASSEMBLY AND METHOD OF USING SAME

TECHNICAL FIELD

The present invention relates in general to a device for securing an intravenous (IV) infusion or injection site of a patient during intravenous infusion or injection and more particularly to a device for securing an intravenous catheter to prevent undesired movement of the catheter thereby decreasing complications and reducing unscheduled catheter restarts.

BACKGROUND

IV's have become a widely used and standard technique to introduce a substance into a vein of an individual. The substance can be introduced rapidly by an intravenous injection, or slowly by an intravenous infusion. IV's are typically used to introduce or administer blood or plasma during a blood transfusion; a mixture of glucose (sugar) and saline (salt) or other varied or concentrated nutrients for artificial feeding or hydration; and various drugs or medicines to treat pain, illness or disease.

IV's are typically comprised of a bag or bottle, a tube and a cannula. The bag or bottle store and contain the substance that is to be administered to the individual and is suspended from a holder above the insertion point of the IV. The tube is generally made of clear plastic for easy examination. The tube is connected at one end to the bag or bottle suspended from the holder. The opposite end of the tube is connected to the cannula. The cannula is inserted into the vein of the individual through the skin at the insertion point. After the cannula is inserted into the vein and connected to the tube, it is generally secured in place by surgical tape to the skin surrounding the insertion point. The cannula is secured in place to prevent damage which could otherwise result from its movement relative to the vein or insertion point through the skin.

An intravenous catheter can be dangerous if not properly secured—dangerous to both the patient and the healthcare worker. Taping the intravenous catheter to the skin of the patient is not an acceptable solution, as tape is not designed to secure a catheter. Moreover, tape allows micro-movement of a catheter which in turn can result in complications, including phlebitis, infiltration, extravasations, dislodgement, disconnection, and even infection. Such complications necessitate unscheduled catheter restarts—which expose healthcare workers to dangerous blood-filled stylets and needles.

An improper angle of insertion can also be dangerous to the patient and can lead to complications such as those described above, particularly phlebitis. Not all insertion sites have the same amount of tissue or flesh surrounding a vein. Therefore, applicant has discovered that a uniform angle of insertion for all sites is not an optimal solution. Moreover, improper insertion angle is difficult to remedy with current application methods.

Therefore it would be highly desirable to have a new and improved device and method for securing an intravenous catheter from unwanted and undesired movement thereby significantly decreasing complications and reducing unscheduled catheter restarts. It would also be desirable to have a new and improved device and method that enables variable angle insertion of intravenous catheters.

SUMMARY

In one embodiment, a venipuncture base plate assembly includes an adapter having a substantially flat retention clip and a platform coupled to the retention clip. The platform includes two or more posts mounted on it. The venipuncture base plate assembly includes a patient interface platform having a base pad and a base unit coupled to the base pad. The base pad can have a bottom surface coated with an adhesive substance. The base unit can include a base plate and a retainer mounted on the base plate that supports the adapter at two or more variable angles relative to the base plate.

In another embodiment, a method of securing an I.V. connected catheter to an individual is described. The method includes coupling a catheter fitting carrying the catheter to an adapter comprising a retention clip having a pair of legs and a pair of laterally projecting protuberances, wherein the pair of legs can be squeezed toward each other. The method also includes coupling the adapter to a patient interface platform having a retainer and a base pad by squeezing the legs of the retention clip while guiding the retention clip into a first pair of opposing channels in the retainer. Finally, the method includes securing the base pad to the individual with an adhesive.

In yet another embodiment, a kit for securing an I.V. connected catheter to an individual is described. The kit includes the following components packaged together: a venipuncture base plate assembly with a patient interface platform having a base pad and a retainer coupled to the base pad, the retainer having at least a first pair of opposing channels; and an adapter with a retention clip having a pair of legs and a pair of laterally projecting protuberances, wherein the pair of legs can be squeezed toward each other.

DESCRIPTION OF DRAWINGS

These and other features and advantages will be apparent from the following more particular description thereof, presented in conjunction with the following drawings, wherein:

FIG. 4 is an exploded view of the venipuncture base plate assembly depicted in FIG. 1.

FIG. 5A is a three-dimensional view of the adapter depicted in FIGS. 1-4.

FIG. 5B is a side elevation view of the adapter depicted in FIGS. 1-5A.

FIG. 5C is a side elevation view of an adapter in accordance with another embodiment.

DETAILED DESCRIPTION

Before discussing the preferred embodiment of the present invention, it may be helpful to first briefly review the basic devices and concepts used in the administration of fluids and or medications directly into a venous system of a patient, which is otherwise called, intravenous therapy, or simply I.V. therapy.

The most common method of administering I.V. fluids is with an I.V. catheter, which generally includes a catheter, a needle, and a catheter head or flashback chamber, which is adapted to be connected to an I.V. set and its associated I.V. tubing by a luer nut arrangement. The flowing of blood into the flashback chamber provides an I.V. technician with a visual indication of a successful venous entry.

In use the I.V. technician or other healthcare provider selects a venous access site, which typically will be the top surface area of a patient's hand or on a surface of the patient's arm. Once the I.V. technician has selected and disinfected the venous access site area, the catheter is then inserted into a located vein within the site area using the needle. The needle is then withdrawn leaving only the semi-flexible catheter in the vein of the patient. Blood flow into the flashback chamber provides the I.V. technician with a visual indication that the catheter has been properly positioned within the vein of the patient.

The I.V. technician then attaches an I.V. fluid set and more particularly, the I.V. tubing to the catheter head using a luer lock nut arrangement disposed at the distal end of the I.V. tubing. The catheter is then typically secured to the patient with surgical tape or some other temporary means of securement.

Figure 1:
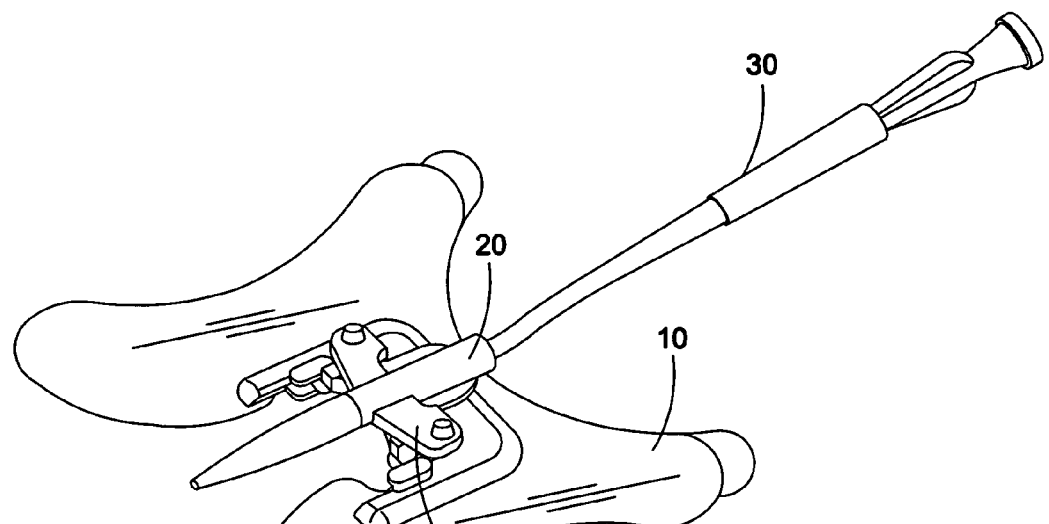
FIG. 1 depicts a three-dimensional view of a venipuncture base plate assembly with a catheter mounted thereon in accordance with one embodiment.
Figure 2:
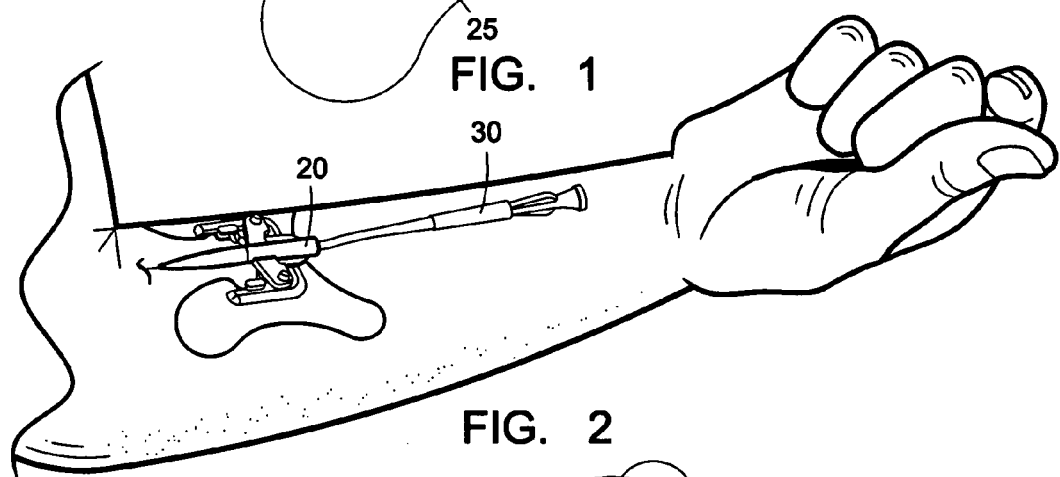
FIG. 2 is an illustration of the venipuncture base plate assembly depicted in FIG. 1 affixed to an arm of a patient.

Referring now to the drawings, and more particularly to FIGS. 1 and 2 thereof, there is illustrated a venipuncture base plate assembly 10 with a catheter fitting 20 carrying a catheter 30 mounted thereon. The venipuncture base plate assembly 10 is depicted with a catheter 30 mounted on the assembly 10 via a semi-standard catheter fitting 20 having wings 25. This type of catheter fitting 20 with a winged configuration is made by several manufacturers, such as Cook, Arrow, Bard, Boston Scientific and B-D. They each have the same winged configuration, but have different dimensions and slightly different geometries.

As shown in FIG. 2, the venipuncture base plate assembly 10 secures the catheter fitting 20 and catheter 30 firmly in place against the patient's skin. Although the venipuncture base plate assembly 10 is placed on a patient's forearm in FIG. 2, the assembly 10 can be placed on any catheter insertion or securement site on the human body, particularly the back of a hand.

Figure 3:
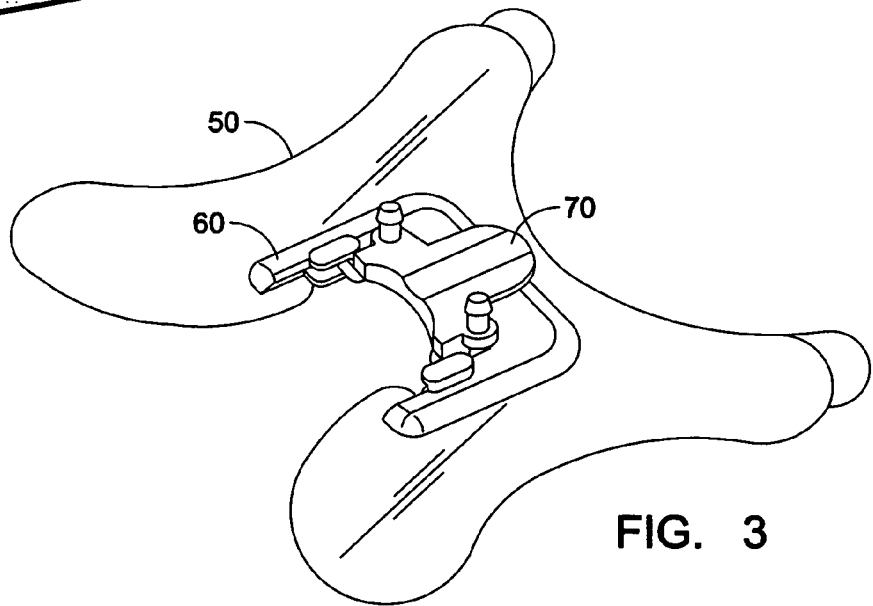
FIG. 3 is a three-dimensional view of a venipuncture base plate assembly.

Turning now to FIGS. 3 and 4, the venipuncture base plate assembly 10 includes a base pad 50, a base plate 60, and an adapter 70 or catheter fitting mount. The catheter 30 is inserted through the catheter fitting 20, which can be mounted onto the adapter 70.

Figure 7:
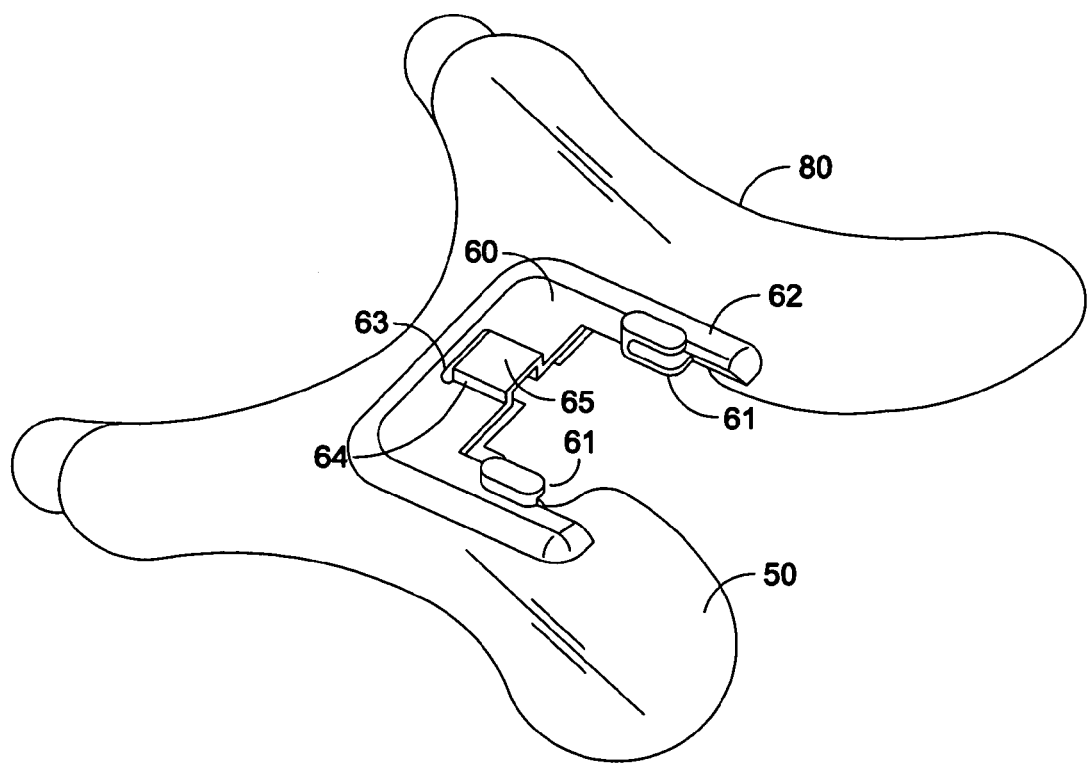
FIG. 7 is a three-dimensional view of a patient interface platform in accordance with one embodiment.

The top surface of the base pad 50 is secured to the bottom surface of the base plate 60 with a non-skin irritating adhesive. Either the bottom surface of the base plate 60 or the top surface of the base pad 50 or both can be coated with the non-skin irritating adhesive. When the base pad 50 and base plate 60 are secured to one another they form a patient interface platform 80, as shown in FIG. 7. The adapter 70 with the catheter fitting 20 and catheter 30 can be demountably connected to the base plate 60 by sliding the alignment pins 71 of the adapter 70 into the two alignment channels 61 of the base plate 60.

Turning now to FIG. 5A, the adapter 70 can be made of a unibody construction for increased durability and strength. Alternatively, the main body of the adapter is made of a unibody construction and the opposing posts 72 are separately forged and secured to the top surface 73 of the adapter using a non-skin irritating adhesive. The main body portion of the adapter 70 includes a top surface 73 and a bottom surface 79.

The main body portion also includes a tongue 78 that protrudes longitudinally in a proximal direction. The tongue 78 supports a catheter body 30, which can rest on the tongue 78. In one embodiment, as shown in the figures, the main body of the adapter 70 includes a cradle 77 that extends longitudinally along the length of the tongue 78. The cradle 77 is shaped to receive a catheter body 30 and prevents the catheter body 30 from tending to roll around atop the adapter 70. In other embodiments, not shown, the tongue 78 has a flat upper surface with no cradle 77.

The adapter 70 also includes a pair of opposing posts 72 that rest atop a pair of wings that extend laterally from opposite sides of the adapter main body. As depicted in FIG. 5, the opposing posts 72 each include a base portion 75 and a flanged head 74. The posts can, however, be shaped differently than what is shown in the figures. For example, the posts 72 can be cone-shaped, frustoconical, pyramid-shaped, or cubical. The posts 72 can be made without bulbous heads 74 so that the tops of the posts are narrower than the bases and the posts are wedged into the holes 22 of the catheter fitting 20. Alternatively, the heads 74 can be spherical, cylindrical, cubical, pyramid-shaped, or any other shape that has a slightly larger cross-section than the base. The posts 72 are about 0.2 inches tall, but can range from about 0.1 inches to about 0.5 inches in height from bottom of the post base 75 to apex or top surface of the post head 74. The base 75 of the posts 72 is about 0.1 inches in height, and the head 74 is also about 0.1 inches in height in one embodiment. The base 75 can range, however, from about 0.05 inches in height to about 0.25 inches in height, while the head can range from about 0.05 inches in height to about 0.25 inches in height.

The adapter 70 also includes opposing alignment pins 71 that extend laterally from opposite sides of the adapter body. The alignment pins 71 are substantially cylindrical, but can also be conical, or pyramid-shaped. They each extend laterally about 0.015 inches from the main body of the adapter 70, but can also extend about 0.01 inches, 0.02 inches, 0.03 inches, or any distance between about 0.01 inches and about 0.1 inches from the main body of the adapter 70.

The adapter can come in various sizes to accommodate various types, brands, and sizes of catheter fittings, such as those already mentioned herein. For example, to accommodate Arrow®, Cook® or Bard® catheter fittings the posts 72 can be set about 0.5 to about 0.6 inches apart from each other; to accommodate a Medcomp® catheter fitting the posts 72 can be set about 0.6 to about 0.7 inches apart from each other; and to accommodate a B-D Boston® catheter fitting the posts 72 can be set about 0.8 to about 0.9 inches apart from each other. In addition, the posts can be set apart from each other at varying distances to accommodate various types, brands, and sizes of catheters. In other embodiments, the posts 72 can be set apart from each other from between about 0.4 inches to about 1.5 inches.

Figure 6:
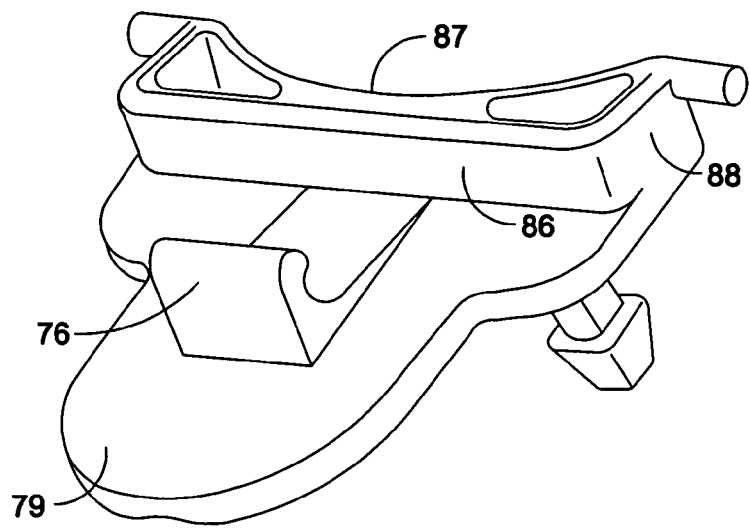
FIG. 6 is an upside-down three-dimensional view of the adapter depicted in FIGS. 1-4.

FIG. 6 shows an underside of the adapter 70. The tip of the tongue 78 forms the proximal end of the adapter, while the distal end is formed by a step 87. The proximal side 86 of the step 87 is about 0.1 inches tall, while the distal side 88 of the step 87 is about 0.07 inches tall. As shown in FIG. 5B, when the adapter 70 is upright, the difference in the height of one side of the step 87 relative to the other side results in an acute angle A between the adapter main body and any flat surface on which the adapter 70 rests. In another embodiment, not shown, the distal side 88 and the proximal side 86 of the step are the same height so that the adapter main body is parallel with any flat surface on which it rests. This embodiment can be used, for example, with the Cook® catheter fitting, which is itself formed with a preset angle.

The underside of the adapter 70 includes a bottom surface 79. Protruding downward from the bottom surface 79 is a lip 76. The lip can be formed from a flat, straight protrusion that is perpendicular to the bottom surface 79 and parallel to the step 87 with a ledge 89 extending distally along the length of its bottom tip as shown in FIG. 5C. The ledge can mate with an indentation 68 at the bottom of the proximal side 63 of the pedestal 64. Alternatively, the lip 76 can bend distally toward the step 87 so that it forms a convex proximal surface and a concave distal surface as shown in FIG. 5B.

Turning now to FIG. 7, the patient interface platform 80 includes the base plate 60 and the base pad 50, which as explained above, are coupled to each other with an adhesive. The base plate 60 includes a proximal shoulder region 66 and a distal region forming two opposing legs 62. The shoulder region 66 includes a pedestal 64 having a top surface 65 and a proximal side surface 63.

Figure 8:
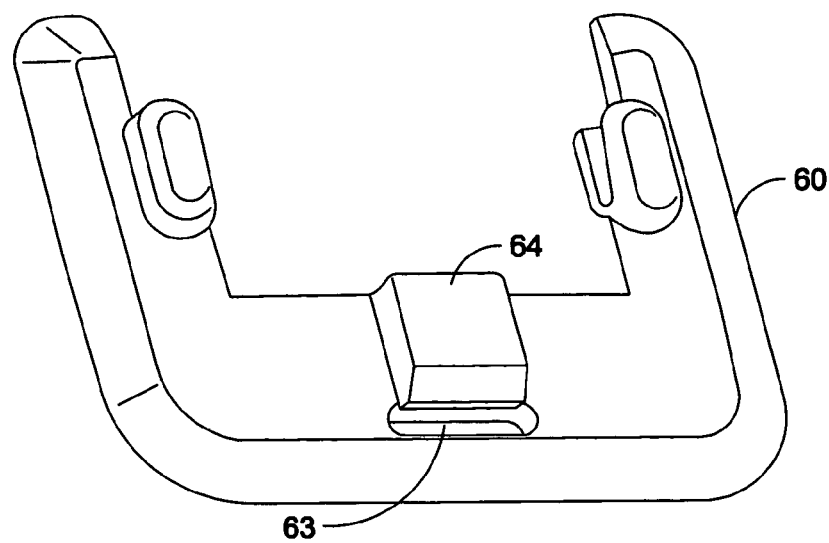
FIG. 8 is a three-dimensional view of a base plate taken from a rear angle in accordance with one embodiment.
Figure 9A:
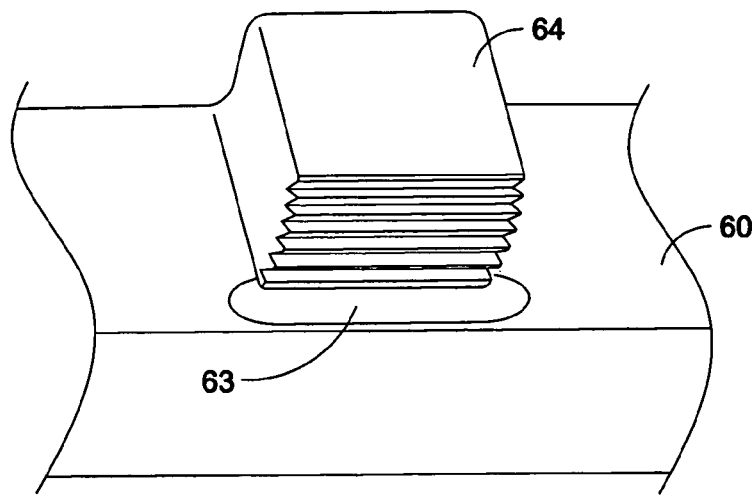
FIG. 9A is an enlarged view of a pedestal of a base plate in accordance with one embodiment.
Figure 9B:
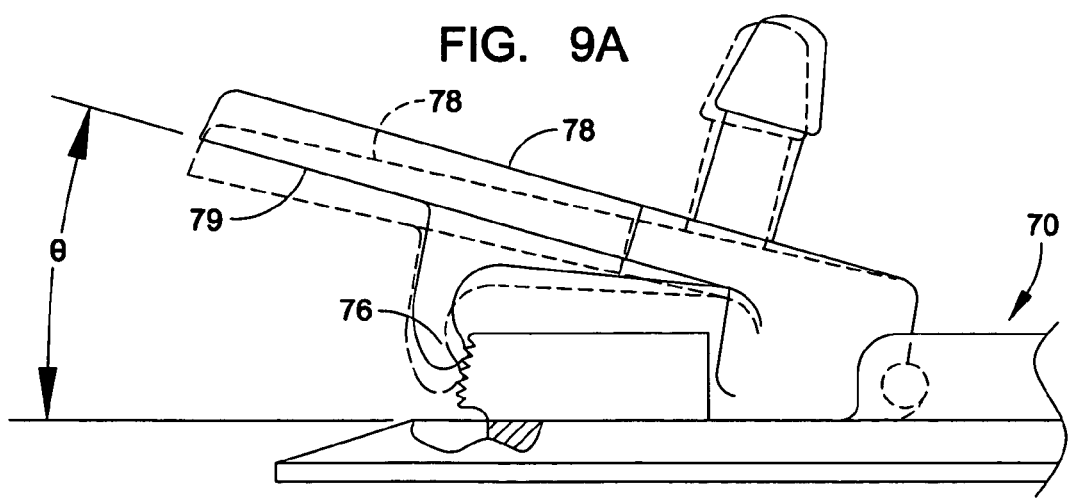
FIG. 9B is a side elevation view of the base plate with the pedestal depicted in FIG. 9A with an adapter mounted thereon.
Figure 10A:
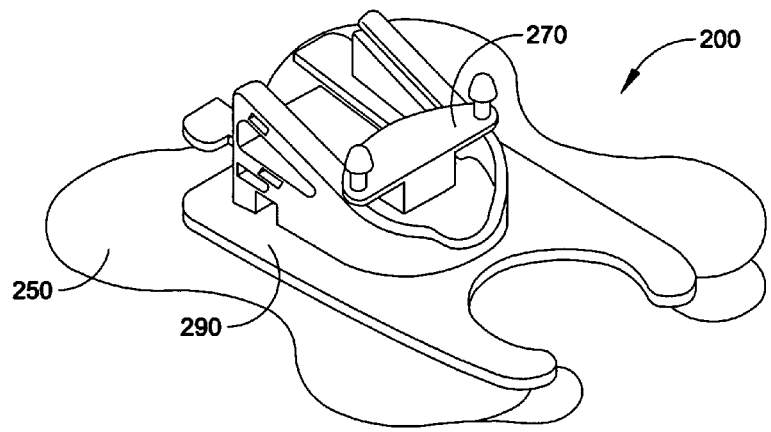
FIGS. 10A-10C depict a venipuncture base plate assembly in accordance with another embodiment.
Figure 10B:
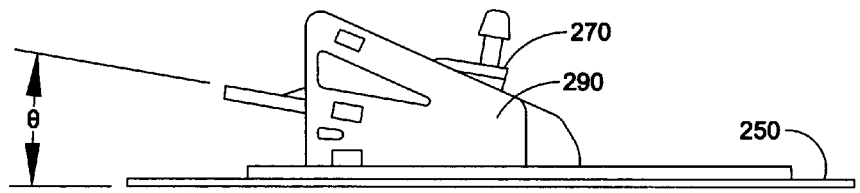
Figure 10C:
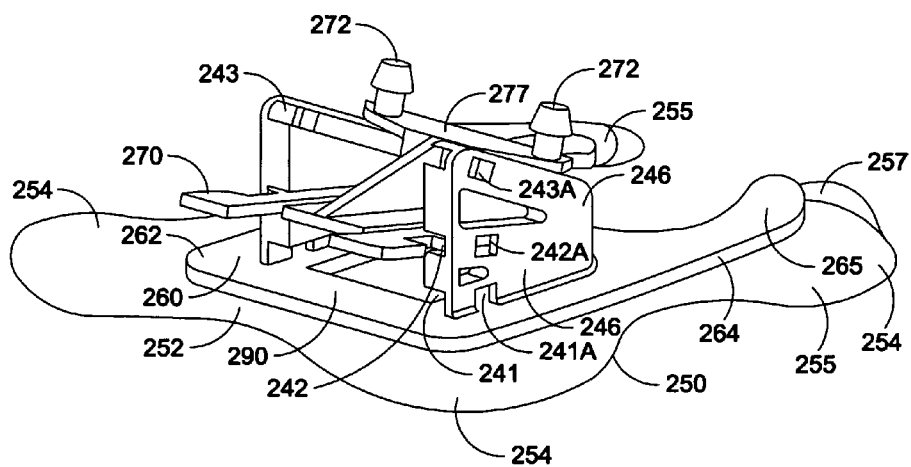
Figure 11:
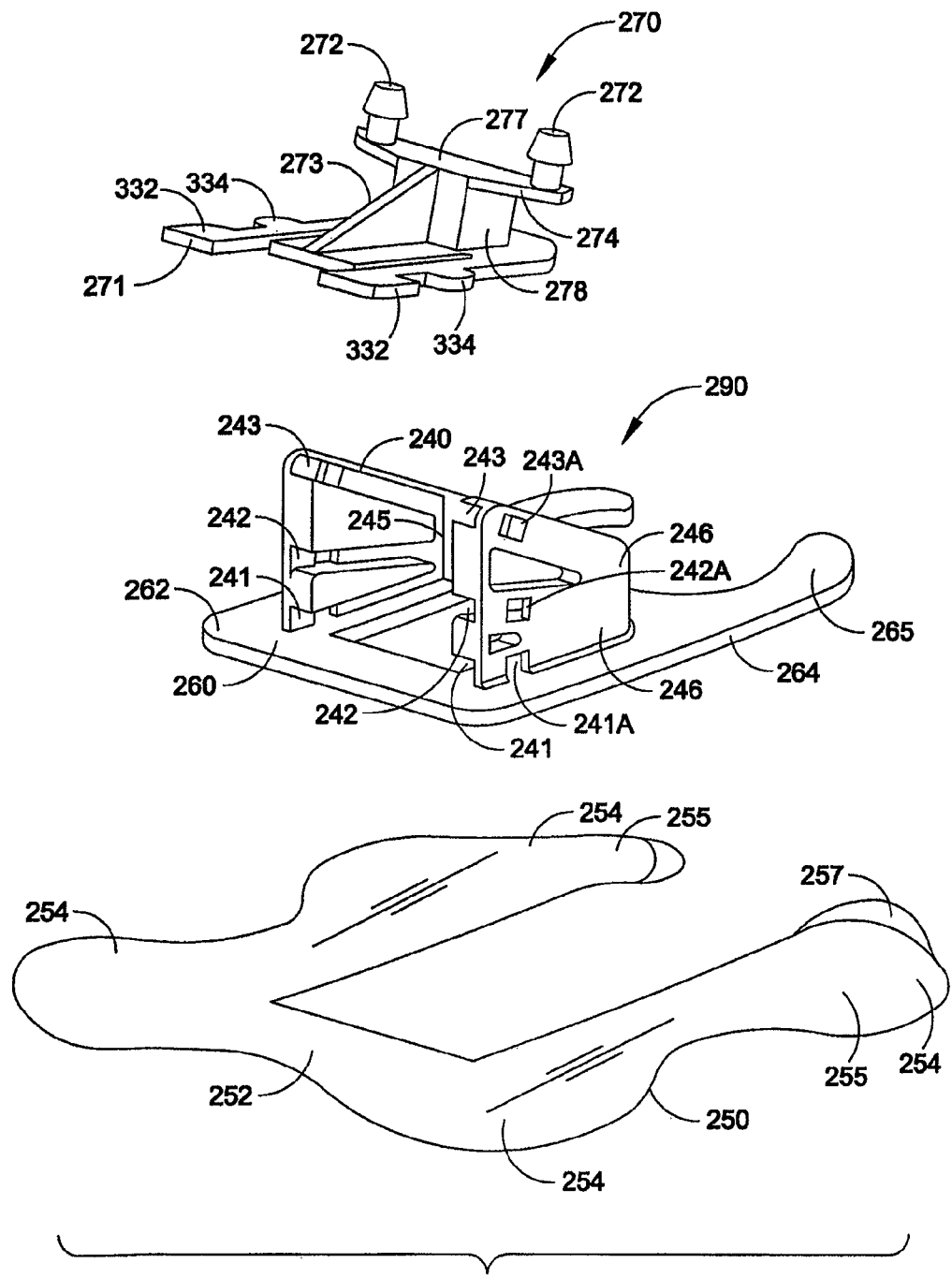
FIG. 11 is an exploded view of the venipuncture base plate assembly depicted in FIGS. 10A-10C.

Turning now to FIGS. 8-9B, the proximal side surface 63 of the pedestal 64 can have a smooth surface. The pedestal 63 forms the support for the adapter 70. After the catheter fitting 20 is mounted onto the adapter 70, the alignment pins 71 of the adapter are guided and slid into the alignment channels 61 of the base. The adapter 70 is pulled or pushed proximally toward the end wall of the alignment channels 71 until the pins 61 snap into place against the end wall of the alignment channels 71. At this point, the adapter is able to pivot about an axis of rotation formed by the pins 61. The tongue 78 of the adapter 70 is pushed down until the lip 76 of the adapter 70 comes into contact with the proximal side surface 63 of the pedestal 64. The adapter 70 is further pushed down until the edge of the lip 76 snaps or locks against the bottom of the proximal side surface 63 of the pedestal. The length of the lip 76 is approximately the same as the height of the pedestal 64 so that when the edge of the lip 76 locks against the bottom of the proximal side surface 63 of the pedestal, the bottom surface of the adapter 70 rests against the top surface 65 of the pedestal. The length of the lip 76 and the height of the pedestal 64 can each be between about 0.05 inches and about 0.5 inches. In one embodiment it is about 0.15 inches. As shown in FIGS. 5B and 5C, the bottom surface of the adapter 70 can form an angled ramp so that it lies flat against the flat top surface 65 of the pedestal 64. Alternatively, the bottom surface of the adapter 70 can be made without an angled ramp, in which case only the distal end of the bottom surface of the adapter 70 near the step will rest against the distal end of the top surface 65 of the pedestal 64.

As can be seen in FIGS. 5B and 5C, the adapter 70 is at an angle θ relative to the base plate 60. This configuration provides a desired angle of attack or inflection for the catheter. Depending on the patient and the anatomy of the insertion site, the length of the lip 76, the corresponding height of the pedestal 64, and the height of the sides of the step 87 can be such that the adapter can be at angle θ between about 5° and about 30° relative to the base plate. In one embodiment, the angle θ is between about 5° and about 10°. In another embodiment, the angle θ is about 10°. In yet another embodiment, the angle θ is about 15°. In yet another embodiment, the angle is about 0° meaning that the adapter 70 and base plate 60 are substantially parallel.

FIGS. 9A and 9B show another embodiment in which the proximal side surface 63 of the pedestal 64 can be crenated so that the teeth of the crenated surface catch against the edge of the lip 76 of the adapter 70. The angle of the adapter 70 body relative to the base plate is therefore variable and adjustable because the alignment pins 71 can rotate within the alignment channels 61 thus changing the angle θ between the base plate and adapter 70 body. The edge of the tongue 76 catches against the teeth of the crenated proximal side surface 63 of the pedestal. Force can be applied to push down on the tongue 78 to reduce the angle θ or an upward force can be applied against the tongue 78 to increase the angle θ depending on the needs of the patient and the most appropriate angle of attack or inflection as determined by the I.V. technician or healthcare provider. The angle θ is adjustable between about 0° and about 30°.

Turning back to FIG. 4, the base pad 50 has a butterfly shape with corners 53 forming two opposing wings. The bottom surface of the base pad 50 is coated with a non-skin irritating adhesive. A wax paper backing 55 covers the bottom surface of the base pad 50 and has a shape that generally matches the butterfly shape of the base pad 50. The surface of the backing 55 is such that it completely covers the bottom surface of the base pad 50. One or more edges of the backing 55 (as shown) extends past the perimeter of the base pad 50 so that it can be easily grasped and peeled away from the base pad 50 prior to placement on the patient. The base pad 50 may include one or more aeration holes or perforations (not shown) to allow air to reach the patient's skin beneath the pad 50. In other embodiments (not shown) the base pad may be rectangular, square, round, oval, or any other shape may be suited for a specific location on the body.

The venipuncture base plate assembly 10 can be packaged as a kit that includes the patient interface platform 80, an adapter 70, and instructions for use (not shown). The kit can be contained in a hermetically sealed package that includes written instructions on the package, inside the package, or separate from the package.

The instructions provide a method of using the venipuncture base plate assembly 10. First, the catheter is introduced into the patient's blood vessel at the insertion site using methods described above and that are well known to those of skill in the art. After the catheter is introduced into the patient's blood vessel, the area around the securement site is cleansed and prepared by removing oil and moisture with an alcohol swab. A skin preparation solution can then be applied for enhanced adherence and skin protection. The holes 22 in the wings 21 of the catheter fitting 20 are then aligned with the posts 72 protruding from the top surface 73 of the adapter 70. The posts 72 are pushed through the holes 22 so that the top portion 74 of the posts snap through the holes 22 of the catheter fitting. The body 24 of the catheter fitting 20 rests against a cradle 77 that is formed on the top surface 73 of the adapter 70. This further reduces the potential for unwanted catheter displacement or movement. The adapter 70 with the catheter fitting 20 now coupled to it is attached to the base plate 60 of the patient interface platform 80. This is accomplished by sliding the opposing alignment pins 71 of the adapter 70 into the opposing alignment channels 61 of the base plate 60. With the alignment pins 71 aligned with the open end of the channels 61, the adapter is pulled or pushed toward the closed back end of the channels 61. The channels 61 may include a bump or protuberance on their inner bottom or top surfaces, which narrows the channel at the region of the protuberance. When the alignment pins 71 are pushed or pulled past the protuberance, they snap into place against the closed back walls of the channels 61. Alternatively, the adapter 70 can be snapped into place by pushing down on the tongue portion 78 of the top surface of the adapter 70 until the lip 76 extending downward from the bottom surface 79 of the adapter 70, slides down along the back side 63 of the pedestal 64 and catches against an indentation at the bottom of the back side 63 of the pedestal 64. Alternatively, the lip 76 can be concave and the back side 63 of the pedestal 64 can be convex so that the two mate. In either case, the bottom surface 79 of the adapter 70 can rest against the top surface 65 of the pedestal 64. Once, the adapter 70 is secured to the patient interface platform 80, the I.V. technician peels away the backing 54 from the underside of the base pad 50 exposing the adhesive layer on the bottom surface of the base pad 50. The base pad 50 is then placed on the securement site of the patient. The corners 53 of the base pad 50 can be padded down by the I.V. technician to further secure the base pad to the skin.

With respect to the embodiment of the base plate shown in FIG. 8, the adjustable adapter 70 can be pushed down or pulled up along the crenated surface 63A of the pedestal 64A to adjust the angle of the adapter 70 relative to the base plate 60, which adjusts the angle of attack of the catheter 30.

Figure 12:
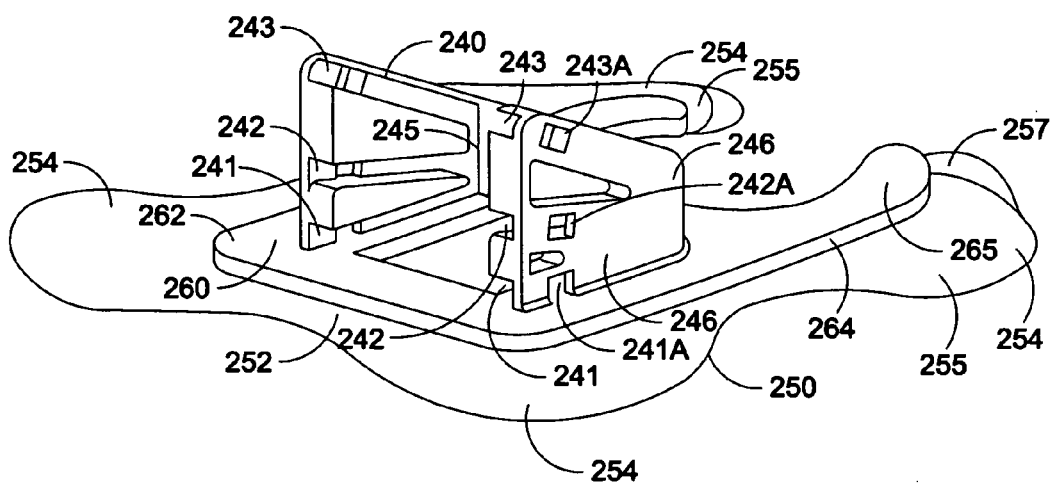
FIG. 12 is three-dimensional view of a patient interface platform in accordance with another embodiment.

Turning now to FIGS. 10A-10C and 11, there is shown another embodiment of a venipuncture base plate assembly 200. The venipuncture base plate assembly includes a base pad 250 a base unit 290, and an adapter 270. The top surface of the base pad 250 is secured to the bottom surface of the base plate 260 of the base unit 290 with a non-skin irritating adhesive. Either the bottom surface of the base plate 260 or the top surface of the base pad 250 or both can be coated with the non-skin irritating adhesive. When the base pad 250 and base plate 260 are secured to one another, the base unit 290 and base pad 250 form a patient interface platform 280, as shown in FIG. 12. The adapter 270 with the catheter fitting 20 and catheter 30 can be demountably connected to the base unit 290 by sliding the retention clip 271 of the adapter 270 into one of the sets of channels 241, 242, or 243 of the retainer 240 on the base unit 290.

The adapter 270 can be made of a unibody construction for increased durability and strength. Alternatively, the retention clip 271, platform 277 and bracket 273 can be separately forged and secured to one another using a non-skin irritating adhesive. The adapter includes a three main components; a retention clip 271, a raised platform 277 carrying opposing posts 272, and a bracket 273.

Figure 13:
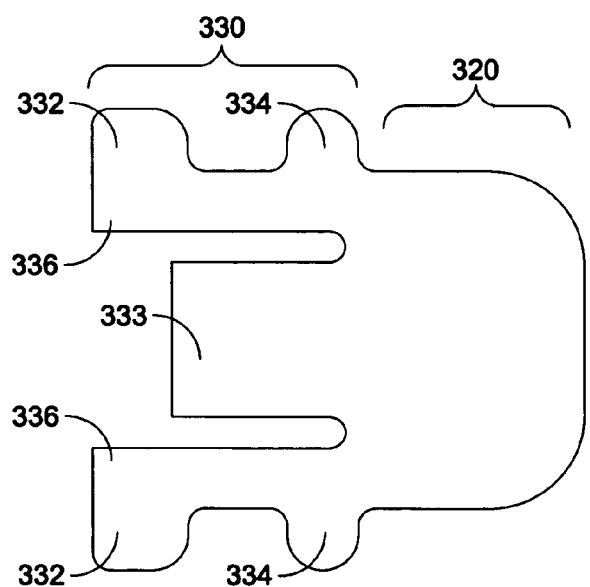
FIG. 13 is a bottom view of the adapter depicted in FIGS. 10A-11.

FIG. 13 shows a bottom view of the adapter 270, predominantly showing the structure of the retention clip 271. The retention clip 271 is a flat structure with a distal region 320 forming rounded corners. The retention clip 271 also has a proximal portion 330 with two proximally projecting legs 332 separated by a central tab 333. The legs each have a pair of protrusions 334 that lock the retention clip 271 into the channels 241, 242, or 243 of the retainer 240 on the base unit 290. The retention clip has a thickness from bottom surface to top surface that is slightly less than the height of the channels 241, 242, and 243 so that the retention clip 271 can easily slide into any of the channels 241, 242, and 243. Although the retention clip 271 is a rigid structure, the legs 332 can be pinched toward each other to lock and unlock the retention clip 271 to the retainer 240.

A raised platform 277 sits atop the top surface of the retention clip 271. The platform 277 includes a base 278 that can be between about 0.1 inches to about 1.5 inches tall. The top of the platform forms a pair of wings 274 that protrude laterally from the base 278. A cradle (not shown) can be formed on the top surface of the raised platform 277 centered between the two posts 272. Atop the pair of wings 274 are a pair of opposing posts 272. The posts 272 can be the same as the posts 72 described with respect to the adapter shown in FIG. 5A. A bracket 273 sits atop the top surface of the retention clip 271. Two sides of the bracket 273 form a right angle with one side flush against the base 278 and the other side flush against the top surface of the retention clip 271. The bracket serves two purposes; it reinforced the connection between the base 278 and the retention clip 271, and it acts as a handle that can be used to carry the adapter between one's fingers and to push and pull the adapter through the channels 241, 242, or 243 of the retainer 240. The bracket 278 can have finger ports or indentations on its sides (not shown) to provide for a comfortable grip.

The base unit 290 includes a base plate 260 and a retainer 240. The base plate 260 includes a proximal region 262 that carries the retainer 240 and a distal region 264 that forms a pair of legs 265 whose ends curve inward toward each other.

The retainer 240 is formed by a pair of walls 246 that sit atop the base plate 260 and are perpendicular to the base plate 260. Each of the walls 246 forms the same trapezoidal shape with the proximal and distal sides being parallel, while the top and bottom sides are not parallel. The walls 246 are mirror images of one another.

Each of the walls 246 has three channels 241, 242, and 243 formed into it. Channels 241 are coplanar, parallel with one another and face each other. Channels 242 are coplanar, parallel with one another and face each other. Channels 243 are coplanar, parallel with one another and face each other. The channels each have an open end on the proximal end of the wall 246 and a closed distal end 245. The floor of the channel 241 is formed by the base plate 260.

The channels 241, 242, and 243 are not parallel with one another. Channel 241 is parallel to a horizontal plane formed by the base plate 260 and/or base pad 250, but the other two channels 242 and 243 are at an angle relative to the base plate 260 and/or base pad 250. In one embodiment, channel 242 is at angle of about 5° relative to the base plate 260 and/or base pad 250, and channel 243 is at an angle of about 15° relative to the base plate 260 and/or base pad 250. In another embodiment, channel 242 is at an angle of about 10° relative to the base plate 260 and/or base pad 250, and channel 243 is at an angle of about 20° relative to the base plate 260 and/or base pad 250. In yet another embodiment, channel 242 is at an angle of about 15° relative to the base plate 260 and/or base pad 250, and channel 243 is at an angle of about 30° relative to the base plate 260 and/or base pad 250. In other embodiments, channel 242 can be at an angle between about 0° and 15° relative to the base plate 260 and/or base pad 250, while the channel 243 can be at an angle between about 15° and about 30° relative to the base plate 260 and/or base pad 250.

In other embodiments (not shown), the retainer can include additional pairs of opposing channels at varying angles relative to the base plate 260. In still other embodiments, the retainer includes only two of the pairs of channels 241, 242, and 243.

Holes 241A, 242A, and 243A are formed into each of the walls 246 of the retainer. Holes 241A correspond and are coplanar with channels 241. Holes 242A correspond and are coplanar with channels 242. Holes 243A correspond and are coplanar with channel 243. The holes 241A, 242A, 243A are sized to receive the protuberances 334 on either side of the retention clip 271. When the retention clip is pushed through the channels 241, 242 or 243 of the retainer 240, the legs 332 of the retention clip 271 are squeezed so that the protuberances 334 fit through and slide along the channels. The retention clip 271 is pushed all the way through the channel and its distal end hits the back wall 245 of the walls 246 the protuberances 334 become aligned with the holes 241A, 242A, or 243A and pop out of those holes, thus securing the retention clip 271 to the retainer 240. If the I.V. technician wants to remove the retention clip, he or she can squeeze the legs 332 together and pull the clip out 271 of the retainer 240.

The base pad 250 has a proximal region 252 that carries the proximal region 262 of the base plate 260 and a pair of legs 255 that carry the pair of legs 265 of the base plate 260. A rectangular open space separates the two legs 255. The base pad has rounded corners 254. The bottom surface of the base pad 250 is coated with a non-skin irritating adhesive. A wax paper backing 257 covers the bottom surface of the base pad 250 and has a shape that generally matches the shape of the base pad 250. The surface of the backing 257 is such that it completely covers the bottom surface of the base pad 250. One or more edges of the backing 257 (as shown) extends past the perimeter of the base pad 250 so that it can be easily grasped and peeled away from the base pad 250 prior to placement on the patient. The base pad 250 may include one or more aeration holes or perforations (not shown) to allow air to reach the patient's skin beneath the pad 250. In other embodiments (not shown) the base pad may be rectangular, square, round, oval, or any other shape may be suited for a specific location on the body.

The venipuncture base plate assembly 200 can be packaged as a kit that includes the patient interface platform 280, an adapter 270, and instructions for use (not shown). The kit can be contained in a hermetically sealed package that includes written instructions on the package, inside the package, or separate from the package.

The instructions provide a method of using the venipuncture base plate assembly 200. First, the catheter is introduced into the patient's blood vessel at the insertion site using methods described above and that are well known to those of skill in the art. After the catheter is introduced into the patient's blood vessel, the area around the securement site is cleansed and prepared by removing oil and moisture with an alcohol swab. A skin preparation solution can then be applied for enhanced adherence and skin protection. The holes 22 in the wings 21 of the catheter fitting 20 are then aligned with the posts 272 protruding from the top surface of the raised platform 277 of the adapter 270. The posts 272 are pushed through the holes 22 so that the top portion of the posts snap through the holes 22 of the catheter fitting. The body 24 of the catheter fitting 20 rests against the raised platform 277 of the adapter 270 and can be cradled by the cradle formed in the raised platform 277 to further secure the catheter fitting 20 and prevent it from unwanted movement. The adapter 270 with the catheter fitting 20 now coupled to it is attached to the base unit 290 of the patient interface platform 280. This is accomplished by sliding the retention clip 271 of the adapter 270 into one of the channels 241, 242, or 243 of the retainer while squeezing the legs 332 of the retention clip 271. The retention clip 271 is pushed into the channel until the protuberances 334 pop into the holes 241A, 242A, or 243A in the walls 246 of the retainer 240 at which point the distal end of the retention clip 271 should abut the closed back wall 245 of the channels.

Once, the adapter 270 is secured to the patient interface platform 280, the I.V. technician peels away the backing 257 from the underside of the base pad 250 exposing the adhesive layer on the bottom surface of the base pad 250. The base pad 250 is then placed on the securement site of the patient. The corners 254 of the base pad 250 can be padded down by the I.V. technician to further secure the base pad to the skin.

If the I.V. technician determines that the catheter's angle of attack is inappropriate, he or she can change the angle of attack by using one of the other channels. The I.V. technician can first remove the catheter fitting 30 from the adapter posts 272. Then the adapter 270 is removed from the retainer 240 by squeezing the legs 332 of the retention clip 271 and pulling the adapter 270 out of the channel in which it resides. The I.V. technician can then guide the retention clip 271 into one of the other channels.

Other embodiments are within the scope of the following claims.

What is claimed is:

1. A securement device for a medical article having at least two holes formed therethrough, the securement device comprising:
   an adapter having a clip and a platform coupled to the clip, the platform comprising two or more posts, the posts being configured to be received by the at least two holes so as to inhibit at least longitudinal motion of a secured portion of the medical article relative to the adapter;
   a base pad having a bottom surface, at least a portion of the bottom surface being coated with an adhesive substance; and
   a retainer supported by the base pad, the retainer configured to fixedly support the adapter at two or more variable angles relative to the bottom surface of the base pad.

2. The securement device of claim 1, wherein the retainer comprises a pair of opposing walls, wherein each of the opposing walls comprises a first guide channel and a second guide channel such that the first guide channels face each other and are coplanar and the second guide channels face each other and are coplanar, and wherein the guide channels are each sized to slidably receive the clip of the adapter.

3. The securement device of claim 2, wherein the first guide channels run at a different angle relative to the bottom surface of the base pad than the second guide channels.

4. The securement device of claim 3, wherein the first guide channels run at angle of about 0° to about 15° relative to the bottom surface of the base pad and the second guide channels run at an angle of about 15° to about 30° relative to the bottom surface of the base pad.

5. The securement device of claim 3, wherein the first guide channels run at an angle of about 0° relative to the bottom surface of the base pad and the second guide channels run at an angle of about 5° relative to the bottom surface of the base pad.

6. The securement device of claim 3, wherein the first guide channels run at an angle of about 5° relative to the bottom surface of the base pad and the second guide channels run at an angle of about 15° relative to the bottom surface of the base pad.

7. The securement device of claim 2, wherein each of the opposing walls comprises a third guide channel formed between the respective wall and a top surface of the retainer such that the third guide channels face each other and are coplaner.

8. The securement device of claim 2, wherein the walls of the retainer comprise holes that correspond with each one of the guide channels, wherein each of said holes is coplanar with its corresponding guide channel.

9. The securement device of claim 8, wherein the clip of the adapter comprises laterally projecting protuberances that fit into said holes at least when said clip is secured to said retainer.

10. The securement device of claim 8, wherein the clip comprises a pair of legs that can be squeezed toward one another.

11. The securement device of claim 1, wherein the platform comprises a cradle configured to receive at least a portion of a catheter fitting.

12. A kit for securing a medical article to an individual comprising the following components packaged together:
- a base pad;
- a retainer supported by the base pad, the retainer having at least a first pair of opposing channels;
- an adapter comprising a clip having a pair of legs and a pair of laterally projecting protuberances, wherein the pair of legs can be squeezed toward each other so as to allow the clip to be slid out of the first pair of opposing channels, and wherein the adapter is selectively supported by the retainer at two or more incident angles; and
- instructions for use according to a method comprising
  - coupling a catheter fitting carrying the catheter to the adapter,
  - coupling the adapter to the retainer by squeezing the legs of the clip while guiding at least a portion of the clip into a first pair of opposing channels in the retainer, and
  - securing the base pad to the individual with an adhesive.

13. A kit for securing a medical article to an individual comprising the following components packaged together:
- a base pad;
- a retainer supported by the base pad, the retainer having at least a first pair of opposing channels;
- an adapter comprising a clip having a pair of legs and a pair of laterally projecting protuberances, wherein the pair of legs can be squeezed toward each other, and wherein the adapter is selectively supported by the retainer at two or more incident angles; and
- instructions for use according to a method comprising
  - coupling a catheter fitting carrying the catheter to the adapter,
  - coupling the adapter to the retainer by squeezing the legs of the clip while guiding at least a portion of the clip into a first pair of opposing channels in the retainer,
  - securing the base pad to the individual with an adhesive,
  - removing the catheter fitting from the adapter,
  - removing the adapter from the retainer by squeezing the legs of the clip and pulling the clip out of the channels,
  - guiding the clip into a second pair of opposing channels in the retainer, wherein the second pair of opposing channels is slanted at a different angle towards the base pad than the first pair of opposing channels, and
  - recoupling the catheter fitting to the adapter.

* * * * *

UNITED STATES PATENT AND TRADEMARK OFFICE
CERTIFICATE OF CORRECTION

PATENT NO. : 8,162,898 B1  
APPLICATION NO. : 11/109480  
DATED : April 24, 2012  
INVENTOR(S) : Clifford A. Wright It is certified that error appears in the above-identified patent and that said Letters Patent is hereby corrected as shown below:

Title Page 3, at Item 56, Column 2, Line 20, Under Other Publications, change "Catheterizatlon" to --Catheterization--.

At Column 3, Line 8-9, Change "and or" to --and/or--.

At Column 10, Line 56, In Claim 7, change "coplaner." to --coplanar.--.

Signed and Sealed this  
Nineteenth Day of March, 2013

Teresa Stanek Rea  
*Acting Director of the United States Patent and Trademark Office*